(12) United States Patent
Uchida et al.

(10) Patent No.: US 7,255,869 B2
(45) Date of Patent: *Aug. 14, 2007

(54) ANHYDROUS COSMETIC COMPOSITIONS CONTAINING POLYOLS

(75) Inventors: Mikio Uchida, Ashiya Hyogo (JP); Misa Azuma, Yao Osaka (JP); Kumiko Nakajima, Kobe Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 97 days.

This patent is subject to a terminal disclaimer.

(21) Appl. No.: 10/273,816

(22) Filed: Oct. 18, 2002

(65) Prior Publication Data

US 2003/0108502 A1    Jun. 12, 2003

Related U.S. Application Data

(60) Provisional application No. 60/340,990, filed on Oct. 30, 2001.

(51) Int. Cl.
 *A61K 9/00*    (2006.01)

(52) U.S. Cl. .................................... 424/401

(58) Field of Classification Search ............. 424/401, 424/70.1, 70.11, 70.27, 400, 402, 405
See application file for complete search history.

(56) References Cited

U.S. PATENT DOCUMENTS

| | | | | |
|---|---|---|---|---|
| 3,250,680 A | 5/1966 | Menkart et al. | ................ | 167/85 |
| 3,723,324 A | 3/1973 | Pierce et al. | .................. | 252/90 |
| 3,958,581 A | 5/1976 | Abegg et al. | .................. | 132/7 |
| 3,962,418 A | 6/1976 | Birkofer | ........................ | 424/70 |
| 4,009,256 A | 2/1977 | Nowak, Jr. et al. | ............ | 424/70 |
| 4,152,416 A | 5/1979 | Spitzer et al. | ................. | 424/46 |
| 4,767,741 A * | 8/1988 | Komor et al. | .................. | 512/3 |
| 5,328,685 A | 7/1994 | Janchitraponvej et al. | .... | 424/71 |
| 5,538,720 A | 7/1996 | Jendryssek-Pfaff et al. | .......... | 424/70.1 |
| 5,554,315 A * | 9/1996 | Tonomura et al. | ........... | 510/535 |
| 5,639,740 A | 6/1997 | Crandall | ...................... | 514/78 |
| 5,902,591 A * | 5/1999 | Herstein | ..................... | 424/401 |
| 6,211,125 B1 | 4/2001 | Crudele et al. | | |
| 6,274,128 B1 | 8/2001 | Bergmann et al. | .......... | 424/70.1 |
| 6,461,623 B2 | 10/2002 | Koike et al. | | |
| 6,540,989 B2 | 4/2003 | Janchitraponvej | .......... | 424/70.1 |
| 6,714,904 B1 | 3/2004 | Torvalds et al. | | |
| 6,730,292 B1 | 5/2004 | Yang et al. | | |
| 6,878,368 B2 | 4/2005 | Ohta et al. | | |
| 2002/0051798 A1 | 5/2002 | Koike et al. | ................. | 424/401 |
| 2003/0017185 A1 | 1/2003 | Koike | | |
| 2003/0103930 A1 | 6/2003 | Uchida et al. | ........... | 424/70.28 |
| 2003/0207817 A1 | 11/2003 | Ide | | |
| 2004/0022823 A1 | 2/2004 | Uchida et al. | .............. | 424/401 |
| 2004/0028711 A1 | 2/2004 | Uchida et al. | .............. | 424/401 |

FOREIGN PATENT DOCUMENTS

| | | |
|---|---|---|
| EP | 0897719 | 2/1999 |
| GB | 1042529 | 9/1996 |
| JP | 06-080534 | 3/1994 |
| JP | 06100411 | 4/1994 |
| JP | 09-087165 | 3/1997 |
| JP | 11228332 A | 8/1999 |
| JP | 11228333 | 8/1999 |
| JP | 2000-302626 | 10/2000 |
| JP | 2001019606 | 1/2001 |
| WO | WO-86 05389 | 9/1986 |
| WO | WO-01-00171 A1 | 1/2001 |
| WO | WO-01 08654 | 2/2001 |
| WO | WO-01 12150 | 2/2001 |

OTHER PUBLICATIONS

Handbook of Cosmetic Science and Technology, 1st Edition, Elsevier Advanced Technology, 1994.*

* cited by examiner

*Primary Examiner*—San-Ming Hui
(74) *Attorney, Agent, or Firm*—Linda M. Sivik; Tara M. Rosnell

(57)    ABSTRACT

Disclosed is anhydrous cosmetic compositions comprising:
  (a) a hydrophobic polyol; and
  (b) a hydrophilic polyol;
which can provide improved conditioning benefits such as moisturizing benefit, and also can provide improved deposition of oily conditioning agents when included in the compositions.

11 Claims, No Drawings

ANHYDROUS COSMETIC COMPOSITIONS CONTAINING POLYOLS

CROSS REFERENCE TO RELATED APPLICATION

The application claims the benefit of U.S. Provisional application Ser. No. 60/340,990 (Case AA573FP), filed on Oct. 30, 2001 in the names of Uchida et al.

TECHNICAL FIELD

The present invention relates to an anhydrous cosmetic composition containing a hydrophobic polyol and a hydrophilic polyol.

BACKGROUND

A variety of cosmetic products such as hair care products and skin care products have been used to the hair and/or skin. With respect to hair care products, for example, hair shampoo products are used for cleansing the hair by removing excess soil and sebum; hair conditioning products are used for providing various conditioning benefits such as moisturized feel, softness, and static control to the hair; hair styling products are used for setting hair style and/or maintaining hair style; hair color products are used for changing hair color and/or maintaining hair color; and hair growth products are used for encouraging hair growth.

The efficacy of cosmetic products such as hair care products and skin care products are changed by various factors, for example, amount of products applied, how long products are applied on the hair, temperatures of products, the way of applying products to the hair, and so on. Thus, it may not be easy to obtain expected efficacy from cosmetic products such as hair care products and skin care products.

Japanese Patent Laid-open 2001-181156 discloses an anhydrous hair rinse composition comprising polyols, cationic surfactants, $C_{14}$-$C_{32}$ fatty alcohols, and silicones, for improving penetration of treatment components to hair by its warming efficacy. Japanese Patent Laid-open 2001-181156 also discloses that; the polyols are, for example, glycerin, propylene glycol, polyethylene glycol, etc.

It has been found that; it is still not easy to obtain expected conditioning efficacy from cosmetic compositions comprising oily conditioning components and hydrophilic polyol carrier. Without intending to be limited by theory, it is believed that; oily conditioning components such as $C_{14}$-$C_{32}$ fatty alcohols and silicones are easily rinsed off from the hair when used together with hydrophilic polyols such as glycerin, propylene glycol, and polyethylene glycol, thus, provide poor deposition on hair.

Based on the foregoing, there remains a desire for obtaining enhanced efficacy from cosmetic products such as hair care products and skin care products, i.e., there remains a desire for obtaining improved benefits from cosmetic products. There also remains a desire for obtaining improved conditioning benefits from cosmetic products.

None of the existing art provides all of the advantages and benefits of the present invention.

SUMMARY

The present invention is directed to an anhydrous cosmetic composition comprising:
(a) a hydrophobic polyol; and
(b) a hydrophilic polyol.

The compositions of the present invention can provide improved conditioning benefits such as moisturizing benefit.

These and other features, aspects, and advantages of the present invention will become evident to those skilled in the art from a reading of the present disclosure.

DETAILED DESCRIPTION

While the specification concludes with claims particularly pointing out and distinctly claiming the invention, it is believed the present invention will be better understood from the following description.

All percentages are by weight of the total composition unless otherwise indicated. All ratios are weight ratios unless otherwise indicated. All percentages, ratios, and levels of ingredients referred to herein are based on the actual amount of the ingredient, and do not include solvents, fillers, or other materials with which the ingredient may be combined as commercially available products, unless otherwise indicated.

As used herein, "comprising" means that other steps and other ingredients which do not affect the end result can be added. This term encompasses the terms "consisting of" and "consisting essentially of".

All cited references are incorporated herein by reference in their entireties. Citation of any reference is not an admission regarding any determination as to its availability as prior art to the claimed invention.

Anhydrous Cosmetic Composition

The anhydrous cosmetic composition comprises hydrophobic polyols and hydrophilic polyols.

It is believed that; hydrophobic polyols can provide improved conditioning benefits such as moisturizing benefit. It is also believed that; hydrophobic polyols can help the deposition of oily conditioning agents when included in the compositions, thus provide improved deposition of oily conditioning agents.

The hydrophobic polyols can be included in the composition at a level by_weight of, preferably from about 2% to about 60%, more preferably from about 5% to about 50%, still preferably from about 10% to about 40% in view of providing conditioning benefits such as moisturizing benefit while providing reduced stickiness. The hydrophilic polyols can be included in the composition at a level by weight of, preferably from about 15% to about 85%, more preferably from about 20% to about 80%, still preferably from about 25% to about 75% in view of the desired viscosity and spreadability of the composition. It is also preferred in the present invention that the hydrophobic polyols and the hydrophilic polyols are included in the composition at a level such that the weight ratio of the hydrophobic polyols to the hydrophilic polyols is from about 1:1 to about 1:50, more preferably from about 1:1.5 to about 1:25, still preferably from_about 1:2 to about 1:10. The ratio is selected in view of providing conditioning benefits such as moisturizing benefit and helping the deposition of oily conditioning agents when included in the composition. It is also preferred in the present invention that the hydrophobic polyols and the hydrophilic polyols are included in the composition at a level such that the sum of the hydrophobic polyols and the hydrophilic polyols is from about 50% to about 98% by weight of the composition in view of the desired viscosity and spreadability of the composition.

Various anhydrous cosmetic compositions such as anhydrous hair care compositions and anhydrous skin care compositions can be used in the present invention. The anhydrous hair care compositions useful herein include, for example, anhydrous hair shampoo compositions, anhydrous hair styling compositions, anhydrous hair conditioning compositions, anhydrous hair color compositions, anhydrous hair growth compositions, and mixtures thereof. The anhydrous skin care compositions useful herein include, for example, anhydrous body shampoo compositions, anhydrous face cleansing compositions, anhydrous skin conditioning compositions, anhydrous shaving compositions, and mixtures thereof. As used in the present invention, "anhydrous" means that the compositions contain 5% or less of water. The anhydrous compositions of the present invention contain, preferably 3% or less of water, more preferably 1% or less of water. Still more preferably, no water is purposely added to the anhydrous composition of the present invention.

The anhydrous cosmetic compositions of the present invention can be in the form of rinse-off products or leave-on products, can be transparent or opaque, and can be formulated in a wide variety of product forms, including but not limited to lotions, creams, gels, emulsions, mousses, and sprays.

The anhydrous cosmetic compositions of the present invention can be mixed with water and applied to the hair and/or skin by any conventional method well known in the art. For example, the anhydrous compositions can be applied to hair and/or skin after mixing with water on hands and/or in a certain vessel. The anhydrous compositions can be applied to wet hair and/or wet skin to mix with water remaining on the hair and/or skin. The anhydrous compositions can be applied to wet and/or dry hair and/or skin to mix with water when rinsed-off.

The anhydrous cosmetic compositions of the present invention can warm by mixing with water. The anhydrous cosmetic compositions of the present invention can warm by a heat from hydrophilic polyols when mixing with water, and can also warm by a heat from inorganic heat generating agents when mixing with water if they are included. The anhydrous cosmetic compositions can warm to a temperature of, preferably from about 25° C. to about 80° C., more preferably from about 30° C. to about 60° C., still more preferably from about 35° C. to about 45° C. This temperature can be adjusted by, for example, the amount of the hydrophilic polyols, the addition of inorganic heat generating agents, choosing the inorganic heat generating agent when added, the amount of the inorganic heat generating agents when added, and additional agents which can control the heat generating reaction. It is believed that; warming cosmetic compositions such as hair care compositions and skin care compositions can provide enhanced efficacy, i.e., can provide improved benefits. With respect to hair care compositions, for example, it is believed that; warming hair shampoo compositions can provide improved cleansing benefits, warming hair styling compositions can provide improved styling benefits, warming hair conditioning compositions can provide improved hair conditioning benefits due to improved penetration of ingredients, warming hair color compositions and warming hair growth compositions can also provide improved benefits. With respect to skin care compositions, for example, it is believed that; warming body shampoo compositions can provide improved cleansing benefits, warming face cleansing compositions can provide improved cleansing benefits, warming skin conditioning compositions can provide improved conditioning benefits, and warming shaving compositions can provide improved shaving benefits.

Hydrophobic Polyol

The anhydrous cosmetic compositions of the present invention comprise hydrophobic polyols. It is believed that hydrophobic polyols can provide improved conditioning benefits such as improved moisturizing benefit. It is also believed that hydrophobic polyols can help the deposition of oily conditioning agents when included in the composition, thus provide improved deposition of oily conditioning agents.

The hydrophobic polyols useful herein are those having a solubility in water at 25° C. of less than about 1 g/100 g water, preferably a solubility in water of less than about 0.5 g/100 g water, and more preferably a solubility in water of less than about 0.1 g/100 g water.

The hydrophobic polyols useful herein preferably have an HLB value of from about 1 to less than about 10, more preferably from about 2 to about 8.

The hydrophobic polyols useful herein can be solid or liquid, preferably liquid at 25° C.

The hydrophobic polyols useful herein include, for example, polypropylene glycols having a molecular weight of from about 200 g/mol to about 100,000 g/mol, $C_2$-$C_{22}$ alkyl ether of polypropylene glycol, polyethylene glycol/polypropylene glycol copolymer, $C_2$-$C_{22}$ alkyl ether of polyethylene glycol/polypropylene glycol copolymer, and mixtures thereof. Some of these hydrophobic polyols can be also used as "POLYOXYALKYLENE DERIVATIVE" described below.

It is understood by the artisan that; depending on the number of propylene units and ethylene units, and the types of copolymers such as random copolymers, block copolymers, and graft copolymers, certain polyethylene glycol/polypropylene glycol copolymers may have a solubility in water at 25° C. of more than about 1 g/100 g water. Such copolymers having a higher water solubility are not intended to be included in this section.

Among these hydrophobic polyols, polypropylene glycol having a molecular weight of from about 200 g/mol to about 100,000 g/mol, is preferably used in the present invention in view of providing conditioning benefits such as moisturizing benefit and helping the deposition of oily conditioning agents when included in the compositions.

Polypropylene Glycol

Polypropylene glycols useful herein are those having a molecular weight of from about 200 g /mol to about 100,000 g/mol, preferably from about 500 g /mol to about 60,000 g/mol, more preferably from about 1,000 g/mol to about 10,000 g/mol, in view of having certain required water solubility and compatibility with hydrophilic polyols. Some polypropylene glycols described herein can also be used as the "VISCOSITY MODIFYING AGENT" described below.

Preferably the polypropylene glycol is selected from the group consisting of a single-polypropylene glycol-chain segment polymer, a multi-polypropylene glycol-chain segment polymer, and mixtures thereof, more preferably selected from the group consisting of a single-polypropylene glycol-chain segment polymer of Formula I, below.

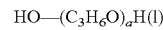

HO—$(C_3H_6O)_a$H(I)

wherein a is a value from about 4 to about 400, preferably from about 10 to about 100, and more preferably from about 20 to about 40.

The single-polypropylene glycol-chain segment polymer useful herein is typically inexpensive, and is readily available from, for example, Sanyo Kasei (Osaka, Japan), Dow Chemicals (Midland, Mich., USA), Calgon Chemical, Inc.

(Skokie, Ill., USA), Arco Chemical Co. (Newton Square Pa., USA), Witco Chemicals Corp. (Greenwich, Conn., USA), and PPG Specialty Chemicals (Gurnee, Ill., USA).

In a preferred embodiment, one or more of the propylene oxide repeating groups in the polypropylene glycol is an isopropyl oxide repeating group. More preferably, substantially all of the propylene oxide repeating groups of the polypropylene glycol are isopropyl oxide repeating groups. Accordingly, a highly preferred single-polypropylene glycol-chain segment polymer has the formula:

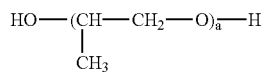

wherein a is defined as described above for Formula I. It is recognized that the isopropyl oxide repeating groups may also correspond either alone, or in combination with the above depicted, to:

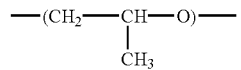

The polypropylene glycol useful herein is readily available from, for example, Sanyo Kasei (Osaka, Japan) as New pol PP-2000, New pol PP-4000.

Multi-polypropylene glycol-chain segment polymer has the formula:

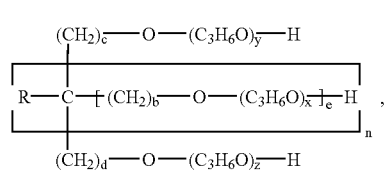 (II)

wherein n is a value from about 0 to about 10, preferably from about 0 to about 7, and more preferably from about 1 to about 4. In Formula II, each R'' is independently selected from the group consisting of H, and $C_1$-$C_{30}$ alkyl, and preferably each R'' is independently selected from the group consisting of H, and $C_1$-$C_4$ alkyl. In Formula II, each b is independently a value from about 0 to about 2, preferably from about 0 to about 1, and more preferably b=0. Similarly, c and d are independently a value from about 0 to about 2, preferably from about 0 to about 1. However, the total of b+c+d is at least about 2, preferably the total of b+c+d is from about 2 to about 3. Each e is independently a value of 0 or 1, if n is from about 1 to about 4, then e is preferably equal to 1. Also in Formula II, x, y, and z is independently a value of from about 1 to about 120, preferably from about 7 to about 100, and more preferably from about 7 to about 100, where x+y+z is greater than about 20.

Examples of the multi-polypropylene glycol-chain segment polymer of Formula II which is especially useful herein includes polyoxypropylene glyceryl ether (n=1, R'=H, b=0, c and d=1, e=1, and x, y, and z independently indicate the degree of polymerization of their respective polypropylene glycol-chain segments; available as New Pol GP-4000, from Sanyo Kasei, Osaka, Japan), polypropylene trimethylol propane (n=1, R'=$C_2H_5$, b=1, c and d=1, e=1, and x, y, and z independently indicate the degree of polymerization of their respective polypropylene glycol-chain segments), polyoxypropylene sorbitol (n=4, each R'=H, b=0, c and d=1, each e=1, and y, z, and each x independently indicate the degree of polymerization of their respective polypropylene glycol-chain segments; available as New Pol SP-4000, from Sanyo Kasei, Osaka, Japan), and PPG-10 butanediol (n=0, c and d=2, and y+z=10; available as Probutyl DB-10, from Croda, Inc., of Parsippany, N.J., U.S.A.).

Hydrophilic Polyol

The anhydrous cosmetic compositions of the present invention comprise hydrophilic polyols. The hydrophilic polyols are preferably used as a carrier in the anhydrous composition of the present invention, and preferably used for generating a heat when mixed with water. The hydrophilic polyols useful herein are preferably liquid at 25° C.

The hydrophilic polyols useful herein are those having a solubility in water at 25° c. of more than about 1 g/100 g water, preferably a solubility in water of more than about 2 g/100 g water, and more preferably a solubility in water of more than about 5 g/100 g water.

The hydrophilic polyols useful herein preferably have an HLB value of about 10 or more.

The hydrophilic polyols useful herein include, for example, polyethylene glycol, propylene glycol, butylene glycol, hexylene glycol, glycerin, diglycerin, diethylene glycol, dipropylene glycol, and mixtures thereof. Among them, preferred are polyethylene glycol, propylene glycol, butylene glycol, hexylene glycol, glycerin, diglycerin, and mixtures thereof. More preferred is polyethylene glycol in view of its ability to generate a heat by mixing with water and physical properties such as viscosity and fluidity.

Polyethylene Glycol

Polyethylene glycol having a variety of molecular weight can be used in the composition of the present invention.

Among them, preferred herein are those having the formula:

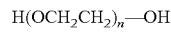

wherein n has an average value of from 4 to 12, and which is a liquid at 25° C. The polyethylene glycol described above is also known as a polyethylene oxide, and polyoxyethylene. Polyethylene glycols useful herein that are especially preferred are PEG-200 wherein n has an average value of about 4. Commercially available preferred polyethylene glycol includes, for example, PEG-200 having trade name Carbowax PEG-200 available from Union Carbide.

High molecular weight polyethylene glycol can be also used in the present invention. The high molecular weight polyethylene glycol can also be used as a conditioning agent, and also used as the "VISCOSITY MODIFYING AGENT" described below. The high molecular weight polyethylene glycols useful herein are those having the formula: $H(OCH_2CH_2)_n$—OH, wherein n has an average value of from 2,000 to 14,000, preferably from about 5,000 to about 9,000, more preferably from about 6,000 to about 8,000. The high molecular weight polyethylene glycols useful herein that are especially preferred are PEG-2M wherein n has an average value of about 2,000 (PEG-2M is also known as Polyox WSR® N-10 from Union Carbide and as PEG-2, 000); PEG-5M wherein n has an average value of about 5,000 (PEG-5M is also known as Polyox WSR® N-35 and as Polyox WSR® N-80, both from Union Carbide and as PEG-5,000 and Polyethylene Glycol 300,000); PEG-7M wherein n has an average value of about 7,000 (PEG-7M is also known as Polyox WSR® N-750 from Union Carbide); PEG-9M wherein n has an average value of about 9,000 (PEG-9M is also known as Polyox WSR® N-3333 from Union Carbide); and PEG-14M wherein n has an average value of about 14,000 (PEG-14M is also known as Polyox WSR® N-3000 from Union Carbide).

Oily Conditioning Agent

The anhydrous cosmetic compositions of the present invention preferably comprise oily conditioning agents. Oily conditioning agents useful herein can be solid or liquid, preferably liquid at 25° C. The oily conditioning agents useful herein has are those having a solubility in water at 25° C. of less than about 1 g/100 g water, preferably a solubility in water of less than about 0.5 g/100 g water, and more preferably a solubility in water of less than about 0.1 g/100 g water.

The oily conditioning agents can be included in the composition at a level by weight of, preferably from about 0.1% to about 20%, more preferably from about 1% to about 10%, still preferably from about 2% to about 10% in view of providing conditioning benefits such as softness and smoothness.

The oily conditioning agents useful herein include, for example, paraffins, esters, silicones, fatty compounds, mineral oils, hydrocarbons, poly α-olefin oils, vegetable oils, and mixtures thereof. Some of these oily conditioning agents can also be used as "CARRIER" described below. Among these oily conditioning agents, preferred are liquid oily conditioning agents and selected from the group consisting of paraffins, esters, silicones, fatty compounds, and mixtures thereof. More preferred are silicone oils in view of providing conditioning benefits such as softness and smoothness.

Ester

Esters preferably used herein are those having a melting point of less than 25° C. Such esters include, for example, pentaerythritol ester oils, trimethylol ester oils, citrate ester oils, glyceryl ester oils, and mixtures thereof. Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO. Particularly useful citrate ester oils herein include triisocetyl citrate with tradename CITMOL 316 available from Bernel, triisostearyl citrate with tradename PELEMOL TISC available from Phoenix, and trioctyidodecyl citrate with tradename CITMOL 320 available from Bernel. Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Silicone

The silicone hereof can include volatile or nonvolatile silicone conditioning agents.

The silicones for use herein preferably have a viscosity of from about 5 to about 2,000,000 centistokes at 25° C., more preferably from about 500 to about 1,800,000, and even more preferably from about 5,000 to about 1,500,000. The viscosity can be measured by means of a glass capillary viscometer as set forth in Dow Corning Corporate Test Method CTM0004, Jul. 20, 1970, which is incorporated by reference herein in its entirety.

Preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. These silicone compounds are available, for example, from GE Toshiba Silicones, from the General Electric Company in their ViscasilR and SF 96 series, and from Dow Corning in their Dow Corning 200 series. Dimethicones having a viscosity of about 10,000 centistokes, for example, from GE Toshiba Silicones with a tradename TSF451-1MA are highly preferred herein.

Another preferred silicone compound is a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference in their entirety. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. These silicone gums are preferably used in the form of mixtures with solvents such as cyclomethicone. Such mixtures have a viscosity of preferably from about 5,000 to about 100,000 centistokes.

Polyalkyleneoxide-modified siloxanes useful herein include, for example, polypropylene oxide modified and polyethylene oxide modified polydimethylsiloxane. The ethylene oxide and polypropylene oxide level should be sufficiently low so as not to interfere with the dispersibility characteristics of the silicone. These materials are also known as dimethicone copolyols.

Amino-substituted siloxanes known as "amodimethicone" are also useful herein. Especially preferred amino-substituted siloxane is a polymer known as "trimethylsilylamodimethicone". Another preferred amino-substituted siloxanes are those having the tradename "UCAR SILICONE ALE 56" available from Union Carbide.

Also useful are silicone resins, which are highly crosslinked polymeric siloxane systems. Preferred resins are offered by General Electric as GE SS4230 and SS4267. Silicone resins in particular, can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetra-functional unit SiO2. The silicone resins for use herein which are preferred are MQ, MT, MTQ, MQ and MDTQ resins. Especially preferred are MQ resins wherein the M:Q ratio is from about 0.5:1.0 to about 1.5:1.0 and the average molecular weight of the resin is from about 1000 to about 10,000.

Fatty Compound

Fatty compounds preferably used herein are those having a melting point of less than 25° C. Such fatty compounds include, for example, unsaturated fatty alcohols having from about 10 to about 30 carbon atoms, unsaturated fatty acids having from about 10 to about 30 carbon atoms, fatty acid derivatives, fatty alcohol derivatives, and mixtures thereof.

Fatty alcohols useful herein include those having from about 10 to about 30 carbon atoms, preferably from about 12 to about 22 carbon atoms, and more preferably from about 16 to about 22 carbon atoms. These fatty alcohols are unsaturated and can be straight or branched chain alcohols. Suitable fatty alcohols include, for example, oleyl alcohol, isostearyl alcohol, tridecylalcohol, decyl tetradecyl alcohol, and octyl dodecyl alcohol. These alcohols are available, for example, from Shinnihon Rika.

Fatty compounds having a melting point of 25° C. or higher can be also used as oily conditioning agents herein. Such fatty compound having a higher melting point can be used as phase changing materials described below under the title "HEAT RESERVING MATERIALS", and also can be used as additional conditioning agents described below under the title "HIGH MELTING POINT FATTY COMPOUND".

Inorganic Heat Generating Agent

The anhydrous cosmetic compositions of the present invention preferably contain an inorganic heat generating agent which generates a heat by mixing with water.

The inorganic heat generating agents useful herein include, for example, chlorides such as calcium chloride ($CaCl_2$, $CaCl_2.H_2O$, $CaCl_2.2H_2O$), magnesium chloride ($MgCl_2$, $MgCl_2.2H_2O$, $MgCl_2.4H_2O$), aluminum chloride ($AlCl_3$, $AlCl_3.6H_2O$), ferric chloride ($FeCl_3$, $FeCl_3.2H_2O$), and zinc chloride ($ZnCl_2$); sulfates such as magnesium sulfate ($MgSO_4$, $MgSO_4.H_2O$, $MgSO_4.4H_2O$), zinc sulfate ($ZnSO_4.H_2O$), ferrous sulfate ($FeSO_4$, $FeSO_4.H_2O$), aluminum sulfate ($Al(SO_4)_3$), calcium sulfate ($CaSO_4$, $CaSO_4.1/2H_2O$, $CaSO_4.H_2O$), and sodium sulfate ($Na_2SO_4$); dry alum; calcium oxide (CaO); magnesium oxide (MgO); sodium carbonate ($Na_2CO_3$); zeolite; and sodium hydrogenphosphate ($Na_2HPO_4$). Preferred are anhydrous inorganic salts such as sodium sulfate ($Na_2SO_4$), calcium sulfate ($CaSO_4$), magnesium sulfate ($MgSO_4$), aluminum sulfate ($Al(SO_4)_3$), calcium chloride ($CaCl_2$), magnesium chloride ($MgCl_2$), calcium oxide (CaO), and mixtures thereof, in view of their effective heat generation, mildness to hair and/or skin, and easy handling. More preferred is anhydrous magnesium sulfate ($MgSO_4$).

The inorganic heat generating agents useful herein have an average diameter of, preferably from about 0.01 μm to about 40 μm, more preferably from about 0.05 μm to about 30 μm, still more preferably from about 0.1 μm to about 20 μm, in view of preventing gritty feel.

The inorganic heat generating agent can be included in the compositions at a level by weight of, preferably from about 5% to about 60%, more preferably from about 5% to about 50%, still more preferably from about 10% to about 45%.

Polyoxyalkylene Derivative

The anhydrous cosmetic compositions of the present invention can contain polyoxyalkylene derivatives. The polyoxyalkylene derivatives are preferably contained in the anhydrous cosmetic composition of the present invention when the composition contains the inorganic heat generating agents. It is believed that; polyoxyalkylene derivatives can help the dispersion of inorganic heat generating agents in carriers, thus, prevent the agglomeration of inorganic heat generating agents which causes gritty feel to the skin and/or hair. It is also believed that; some of the polyoxyalkylene derivatives can provide slippery feel which eases gritty feel caused by inorganic heat generating agents.

The polyoxyalkylene derivatives useful herein are preferably water soluble polyoxyalkylene derivatives.

The polyoxyalkylene derivatives useful herein include, for example, polyoxyethylene/polyoxypropylene copolymer, polyoxyethylene alkyl ether, polyoxypropylene alkyl ether, polyoxyethylene alkyl ether ester, polyoxypropylene alkyl ether ester, polyoxyethylene glyceryl ester, polyoxypropylene glyceryl ester, and mixtures thereof. Some of these polyoxyalkylene derivatives can be also used as "HYDROPHOBIC POLYOL" described above. Among them, polyoxyethylene/polyoxypropylene copolymers are preferably used in view of preventing agglomeration of inorganic heat generating agents, and polyoxyethylene glyceryl esters are preferably used in view of providing slippery feel.

The polyoxyalkylene derivative can be included in the compositions at a level by weight of, preferably from about 0.1% to about 10%, more preferably from about 0.5% to about 10%, still more preferably from about 1% to about 5%.

Polyoxyethylene/polyoxypropylene Copolymer

Preferred polyoxyethylene/polyoxypropylene copolymers include, for example, polyoxyethylene/polyoxypropylene random copolymer and polyoxyethylene/polyoxypropylene block copolymer.

Among these polyoxyalkylene derivatives, polyoxyethylene/polyoxypropylene copolymers including polyoxyethylene/polyoxypropylene random copolymer and polyoxyethylene/polyoxypropylene block copolymer are preferably used in the composition of the present invention in view of their suspending benefit. More preferred is polyoxyethylene/polyoxypropylene block copolymer, still more preferred is polyoxyethylene/polyoxypropylene block copolymer having a weight ratio of polyoxyethylene to polyoxypropylene of from about 5:10 to about 8:10, even more preferred is the block copolymer having the ratio of 8:10.

Commercially available polyoxyalkylene derivatives useful herein include: polyoxyethylene/polyoxypropylene block copolymer; having CTFA name Poloxamer 338, available from BASF under trade name Pluronic F-108, and also available from Sanyo Chemical under trade name Newpol PE-108; and having CTFA name Poloxamer 288, available from BASF under trade name Pluronic F-98, and also available from Sanyo Chemical under trade name Newpol PE-98.

Polyoxyethylene Glyceryl Ester

Preferred polyoxyethylene glyceryl esters include, for example, PEG-modified triglycerides with tradenames Tagat TO®, Tegosoft GC, Tagat BL 276®, Tagat S®, Tagat S 2® (all manufactured by Goldschmidt Chemical Corporation) and with tradenames Crovol A-40, Crovol M-40 (manufactured by Croda Corporation); and PEG-modified glyceryl fatty acid esters such as PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil, PEG-30 stearate, PEG-40 stearate, PEG-50 stearate, PEG-75 stearate, PEG-90 stearate, PEG-100 stearate, PEG-120 stearate, and PEG-150 stearate. Among these esters, more preferred are the PEG-modified triglycerides.

Carrier

In the anhydrous cosmetic composition of the present invention, the hydrophilic polyols are preferably used as a carrier. The anhydrous cosmetic composition of the present invention may contain additional carrier other than the hydrophilic polyols.

The additional carriers useful herein are liquid carriers and include; for example, liquid paraffin; mineral oil; vegetable oil; ester oil such as pentaerythritol tetraisostearate; and mixtures thereof. These additional carriers can be used as the "OILY CONDITIONING AGENT" described above.

The carrier can be included in the compositions at a level by weight of, preferably from about 10% to about 90%, more preferably from about 25% to about 90%, still more preferably from about 30% to about 85%.

Reaction Control Agent

The anhydrous cosmetic compositions of the present invention may contain reaction control agents which can control the heat generating reaction of the inorganic heat generating agent. The reaction control agents may slow down the reaction, or accelerate the reaction. The reaction control agents may also control the temperature to which the cosmetic composition warms up.

Acids can be used as reaction control agents for accelerating the reaction of the inorganic heat generating agents. The acid useful herein includes, for example, citric acid, sodium diphosphate, potassium diphophate, l-glutamic acid, lactic acid, hydrochloric acid, malic acid, succinic acid, acetic acid, fumaric acid, l-glutamic acid hydrochloride, tartaric acid, and mixtures thereof; preferably l-glutamic acid, lactic acid, hydrochloric acid, and mixtures thereof. Among the above acids, citric acid is preferably used herein. Some acids can also be used together with amidoamines for providing conditioning benefits as described below. The acid can be contained at a level such that the mole ratio of the inorganic heat generating agent to acid is from about 1:0.1 to about 1:10, preferably from about 1:0.5 to about 1:5.

Water absorbing polymer can be used as reaction control agents for slowing down the reaction of the inorganic heat generating agent. The water absorbing polymer useful herein includes, for example, vinyl polymers such as cross linked acrylic acid polymers with the CTFA name Carbomer, carboxylic acid/carboxylate copolymers such as acrylic acid/alkyl acrylate copolymers with the CTFA name Acrylates/C10-30 Alkyl Acrylate Crosspolymer, cellulose derivatives and modified cellulose polymers such as Hydroxyethylcellulose and Hydroxypropyl cellulose, polyvinylpyrrolidone, polyvinyl alcohol, guar gum, other gums, starch-based polymers, alginic acid-based polymers, acrylate polymers, polyalkylene glycols having a molecular weight of more than about 1000, and mixtures thereof. These water absorbing polymers can also be used as the "VISCOSITY MODIFYING AGENT" described below. Among the above water absorbing polymers, preferred are cellulose derivatives and modified cellulose polymers, and more preferred is Hydroxyethylcellulose. The water absorbing polymers can be included in the compositions at a level by weight of, preferably from about 0.2% to about 20%, more preferably from about 0.5% to about 15%, still more preferably from about 1% to about 10%.

Heat Reserving Material

The anhydrous cosmetic compositions of the present invention may contain heat reserving materials which can reserve a heat. The heat reserving material can be used for prolonging heating, and may be used for slowing down the warming speed, and may also control the temperature to which the cosmetic composition warms up.

The heat reserving materials include, for example, silica gel, carboxymethyl cellulose gel, phase-changing materials, and mixtures thereof. The phase-changing materials useful herein are those which have a melting point of from about 25° C. to about 80° C. The phase-changing materials useful herein include, for example, a fatty compound such as fatty alcohol and fatty acid; hydrocarbons; a mixture of hydrocarbons and foamed polyolefin; and mixtures thereof. Fatty compound useful herein are described below under the title "HIGH MELTING POINT FATTY COMPOUND", and can also be used as the "OILY CONDITIONING AGENT" described above.

The heat reserving material can be included in the compositions at a level by weight of, preferably from about 0.2% to about 20%, more preferably from about 0.5% to about 15% still more preferably from about 1% to about 10%.

Viscosity Modifying Agent

The anhydrous cosmetic composition of the present invention may contain a viscosity modifying agent. The viscosity modifying agent useful herein includes, for example, vinyl polymers such as cross linked acrylic acid polymers with the CTFA name Carbomer, carboxylic acid/carboxylate copolymers such as acrylic acid/alkyl acrylate copolymers with the CTFA name Acrylates/C10-30 Alkyl Acrylate Crosspolymer, cellulose derivatives and modified cellulose polymers, polyvinylpyrrolidone, polyvinyl alcohol, guar gum, other gums, starch-based polymers, alginic acid-based polymers, acrylate polymers, polyalkylene glycols having a molecular weight of more than about 1000, inorganic water soluble material such as bentonite, aluminum magnesium silicate, laponite, hectorite, and anhydrous silicic acid, and mixtures thereof. The polymers described herein can also be used as the "REACTION CONTROL AGENT" described above. Some polyalkylene glycols described herein can also be used as the "HYDROPHOBIC POLYOL" or "HYDROPHILIC POLYOL" described above.

The viscosity modifying agent can be included in the compositions at a level by weight of, preferably from about 0.01% to about 5%, more preferably from about 0.05% to about 3% still more preferably from about 0.1% to about 3%.

Hair Conditioning Composition

The anhydrous cosmetic compositions of the present invention are preferably anhydrous hair care compositions, more preferably anhydrous hair conditioning compositions. The anhydrous hair conditioning compositions preferably comprise the above described oily conditioning agents in addition to the above described hydrophobic polyols and hydrophilic polyols. The anhydrous hair conditioning compositions can further contain additional conditioning agents, for example, high melting point fatty compounds, cationic conditioning agents such as cationic surfactants and cationic polymers, and mixtures thereof. Among these additional conditioning agents, preferred are high melting point fatty compounds, cationic surfactants, and mixtures thereof.

High Melting Point Fatty Compound

The hair conditioning composition of the present invention preferably comprises a high melting point fatty compound. The high melting point fatty compound can be used as the phase changing materials described above under the title "HEAT RESERVING MATERIALS", and can also be used as the "OILY CONDITIONING AGENT" described above.

The high melting point fatty compound useful herein have a melting point of 25° C. or higher, and is selected from the group consisting of fatty alcohols, fatty acids, fatty alcohol derivatives, fatty acid derivatives, and mixtures thereof. Further, it is understood by the artisan that, depending on the number and position of double bonds, and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

The high melting point fatty compound can be included in the composition at a level by weight of, preferably from about 0.1% to about 30%, more preferably from about 0.2% to about 25%, still more preferably from about 0.5% to about 15%.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include, cetyl alcohol, stearyl alcohol, behenyl alcohol, and mixtures thereof.

The fatty acids useful herein are those having from about 10 to about 30 carbon atoms, preferably from about 12 to about 22 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

Commercially available high melting point fatty compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy).

Cationic Surfactant

The hair conditioning composition of the present invention may contain a cationic surfactant. The cationic surfactant can be included in the composition at a level by weight of, preferably from about 0.1% to about 10%, more preferably from about 0.25% to about 8%, still more preferably from about 0.5% to about 5%.

Nonlimiting examples of preferred cationic surfactants include: behenyl trimethyl ammonium chloride available, for example, with tradename INCROQUAT TMC-80 from Croda and ECONOL TM22 from Sanyo Kasei, distearyl dimethyl ammonium chloride available, for example, with tradename Varisoft TA 100 from Goldschmidt, cetyl trimethyl ammonium chloride available, for example, with tradename CA-2350 from Nikko Chemicals, hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Other cationic surfactants can be also used in the present invention. Such cationic surfactants are quaternary ammonium compound having at least one group selected from the group consisting of an ester group, an amido group, and mixtures thereof. Nonlimiting examples of these cationic surfactants are di-(alkyl carboxyethyl) hydroxyethyl methylammonium methosulfate with a tradename Rewoquat V3620 available from Goldschmidt, and methyl bis-(alkylamidoethyl) 2-hydroxyethylammonium methosulfate with a tradename Varisoft 222 LT-90 available from Goldschmidt.

Salts of amidoamines and acids can be used as cationic surfactants. The amidoamine useful herein are those having the following general formula:

$$R^1CONH(CH_2)_mN(R^2)_2$$

wherein $R^1$ is a residue of $C_{11}$ to $C_{24}$ fatty acids, $R^2$ is a $C_1$ to $C_4$ alkyl, and m is an integer from 1 to 4. Preferred amidoamines useful in the present invention includes stearamidopropyidimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyidiethylamine, behenamidoethyldiethylamine, behenamidoethyidimethylamine, arachidamidopropyldimethylamine, arachidamidopropyldiethylamine, arachidamidoethyidiethylamine, arachidamidoethyldimethylamine, and mixtures thereof; more preferably stearamidopropyidimethylamine, stearamidoethyldiethylamine, and mixtures thereof. Commercially available amidoamines useful herein include: stearamidopropyldimethylamine having tradename SAPDMA available from Inolex, and tradename Amidoamine MPS available from Nikko. The acids useful herein are selected from the group consisting of l-glutamic acid, lactic acid, hydrochloric acid, malic acid, succinic acid, acetic acid, fumaric acid, l-glutamic acid hydrochloride, tartaric acid, and mixtures thereof; preferably l-glutamic acid, lactic acid, hydrochloric acid, and mixtures thereof. The acid described herein can also be used as the "REACTION CONTROL AGENTS" described above. The acid can be contained at a level such that the mole ratio of amidoamine to acid is, preferably from about 1:0.3 to about 1:1, more preferably from about 1:0.5 to about 1:0.9. Commercially available acids useful herein include: l-Glutamic acid: l-Glutamic acid (cosmetic grade) available from Ajinomoto.

Nonionic Surfactant

The anhydrous hair care composition of the present invention preferably contains nonionic surfactant in view of providing a physical stability. The nonionic surfactant can be included in the composition of the present invention at a level by weight of, preferably from about 0.01% to about 10%, more preferably from about 0.05% to about 8%, still preferably from about 0.1% to about 5%.

The nonionic surfactant useful herein includes, for example, polyoxyethylene glyceryl esters such as PEG-modified triglycerides with tradenames Tagat TO® available from Goldschmidt Chemical Corporation, PEG-60 hydrogenated castor oil, and PEG-100 stearate; ethylene glycol ethers of fatty alcohols such as ceteareth-20; alkyl polysaccharide surfactants such as alkyl polyglycosides; long chain tertiary amine oxides such as lauramine oxide; and long chain tertiary phosphine oxides such as lauryl dimethyl phosphine oxide. Polyoxyethylene glyceryl esters useful herein are described above under the title "POLYOXYALKYLENE DERIVATIVE". Among them, preferred are polyoxyethylene glyceryl esters and ethylene glycol ethers of fatty alcohols.

Additonal Components

The hair conditioning composition of the present invention may include other additional components, which may be selected by the artisan according to the desired characteristics of the final product and which are suitable for rendering the composition more cosmetically or aesthetically acceptable or to provide them with additional usage benefits.

A wide variety of other additional components can be formulated into the present compositions. These include: other conditioning agents such as hydrolyzed collagen with tradename Peptein 2000 available from Hormel, vitamin E with tradename Emix-d available from Eisai, panthenol available from Roche, panthenyl ethyl ether available from Roche, a mixture of Polysorbate 60 and Cetearyl Alcohol with tradename Polawax NF available from Croda Chemicals, glycerylmonostearate available from Stepan Chemicals, hydroxyethyl cellulose available from Aqualon, 3-pyridinecarboxy acid amide (niacinamide), hydrolysed keratin, proteins, plant extracts, and nutrients; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; and sequestering agents, such as disodium ethylenediamine tetra-acetate; ultraviolet and infrared screening and absorbing agents such as octyl salicylate, antidandruff agents such as zinc pyridinethione, and salicylic acid; and optical brighteners, for example polystyrylstilbenes, triazinstilbenes, hydroxycoumarins, aminocoumarins, triazoles, pyrazolines, oxazoles, pyrenes, porphyrins, imidazoles, and mixtures thereof; non-heat generating particles such as cellulose particles, mica, silica, mud, clay, and mixtures thereof.

Other additional components generally are used individually at levels of from about 0.001% to about 10%, preferably up to about 5% by weight of the composition.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below.

All percentages herein are based upon the total weight of the compositions, and all such weight percentages as they pertain to listed ingredients are based on the active level and, therefore, do not include carriers or by-products that may be included in commercially available materials.

| | Hair Conditioning Compositions | | | | | | | | | |
|---|---|---|---|---|---|---|---|---|---|---|
| Components | Ex. 1 | Ex. 2 | Ex. 3 | Ex. 4 | Ex. 5 | Ex. 6 | Ex. 7 | Ex. 8 | Ex. 9 | Ex. 10 |
| Polyethylene glycol *1 | q.s. to 100% | q.s. to 100% | q.s. to 100% | q.s. to 100% | q.s. to 100% | — | — | 5.0 | 10.0 | 30.0 |
| Propyleneglycol | — | — | — | — | 5.0 | q.s. to 100% | q.s. to 100% | q.s. to 100% | q.s. to 100% | q.s. to 100% |
| Polypropylene glycol *2 | 19.3 | 10.0 | 19.3 | 19.3 | 10.0 | 19.3 | 10.0 | 19.3 | 19.3 | 19.3 |
| Silicone oil *3 | 4.2 | 1.0 | 4.2 | 4.2 | — | — | 4.2 | — | 2.1 | 4.2 |
| Ester oil *4 | — | — | — | — | 2.0 | — | — | 2.0 | 1.0 | 1.0 |

-continued

Hair Conditioning Compositions

| Components | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Anhydrous magnesium sulfate (MgSO$_4$) | 15.0 | 25.0 | 15.0 | — | 15.0 | 15.0 | 25.0 | 15.0 | 15.0 | 15.0 |
| Polyethylene/polypropylene block copolymer *5 | 3.0 | 3.0 | 3.0 | — | 3.0 | 3.0 | 3.0 | 3.0 | — | 3.0 |
| Cetyl Alcohol *6 | 1.0 | 3.6 | 1.0 | 1.0 | 1.0 | 1.0 | 1.0 | 2.0 | 1.0 | 2.0 |
| Stearyl Alcohol *7 | 1.8 | 6.1 | 1.8 | 1.8 | 1.8 | 1.8 | 1.8 | 3.6 | 1.8 | 3.6 |
| Behenyl trimonium chloride *8 | 0.8 | 2.0 | 0.8 | 0.8 | 2.0 | 0.8 | 0.8 | 1.6 | 0.8 | 1.6 |
| Distearyl dimethyl ammonium chloride *9 | 0.8 | 2.0 | 0.8 | 0.8 | — | 0.8 | 0.8 | 1.6 | 0.8 | 0.8 |
| Di-(alkyl carboxyethyl) hydroxyethyl methylammonium methosulfate *10 | 1.7 | — | 1.7 | — | 1.7 | 1.7 | — | — | 1.7 | 1.7 |
| Stearamidopropyl Dimethylamine *11 | — | — | 0.8 | 0.8 | — | — | — | 2.0 | — | — |
| l-Glutamic acid *12 | — | — | 0.25 | 0.25 | — | — | — | 0.25 | — | — |
| Hydroxyethylcellulose *13 | — | — | 0.5 | — | — | — | 0.5 | — | — | — |
| PEG modified glyceride *14 | — | 5.0 | — | 5.0 | — | — | — | 5.0 | 5.0 | — |
| Perfume | 0.3 | 0.3 | 0.3 | 0.3 | 0.3 | 0.3 | 0.3 | 0.3 | 0.3 | 0.3 |
| Methyl paraben | 0.2 | 0.2 | 0.2 | 0.2 | 0.2 | 0.2 | 0.2 | 0.2 | 0.2 | 0.2 |
| Propyl paraben | 0.1 | 0.1 | 0.1 | 0.1 | 0.1 | 0.1 | 0.1 | 0.1 | 0.1 | 0.1 |
| 3-pyridinecarboxy acid amide | — | 0.05 | 0.05 | 0.05 | 0.05 | — | 0.05 | 0.05 | 0.05 | 0.05 |
| dl-Alpha tocopherol acetate | — | 0.05 | 0.05 | 0.05 | 0.05 | — | 0.05 | 0.05 | 0.05 | 0.05 |
| Hydrolyzed collagen *15 | — | 0.01 | 0.01 | 0.01 | 0.01 | — | 0.01 | 0.01 | 0.01 | 0.01 |
| Panthenol *16 | — | 0.05 | 0.05 | 0.05 | 0.05 | — | 0.05 | 0.05 | 0.05 | 0.05 |
| Panthenyl Ethyl Ether *17 | — | 0.05 | 0.05 | 0.05 | 0.05 | — | 0.05 | 0.05 | 0.05 | 0.05 |
| Octyl methoxycinnamate | — | 0.09 | 0.09 | 0.09 | 0.09 | — | 0.09 | 0.09 | 0.09 | 0.09 |
| Benzophenone-3 | — | 0.09 | 0.09 | 0.09 | 0.09 | — | 0.09 | 0.09 | 0.09 | 0.09 |

Definitions of Components
*1 Polyethylene glycol: Carbowax PEG-200 available from Union Carbide.
*2 Polypropylene Glycol: PPG-34 having a tradename PP2000 available from Sanyo Kasei.
*3 Silicone oil: Dimethicone having a viscosity of about 10,000 centistokes having a tradename T5F451-1MA available from GE Toshiba Silicone.
*4 Ester oil: Pentaerythritol Tetraisostearate having a tradename KAK PTI available from Kokyu alcohol.
*5 Polyethylene/polypropylene block copolymer: Poloxamer 338 having a tradename Newpol PE-108 available from Sanyo Chemical.
*6 Cetyl Alcohol: Konol series available from Shin Nihon Rika.
*7 Stearyl Alcohol: Konol series available from Shin Nihon Rika.
*8 Behenyl trimonium chloride: Econol TM-22 available from Sanyo Kasei.
*9 Distearyl dimethyl ammonium chloride: Varisoft TA100 available from Goldschmidt.
*10 Di-(alkyl carboxyethyl) hydroxyethyl methylammonium methosulfate: Rewoquat V3620 available from Goldschmidt.
*11 Stearamidopropyl Dimethylamine: SAPDMA available from Inolex.
*12 l-Glutamic acid: l-Glutamic acid (cosmetic grade) available from Ajinomoto.
*13 Hydroxyethylcellulose: Natrosol 250 MBR available from Hercules.
*14 PEG modified glyceride: Tagat TO available from Goldschmidt.
*15 Hydrolyzed collagen: Peptein 2000 available from Hormel.
*16 Panthenol: available from Roche.
*17 Panthenyl Ethyl Ether: available from Roche.

Method of Preparation

The hair conditioning compositions of Examples 1 through 10 as shown above can be prepared by any conventional method well known in the art. They are suitably made as follows: Hydrophobic polyols, and when included in the composition, PEG modified glyceride, and other carriers are added to hydrophilic alcohol to make a mixture. When included in the composition, polymeric materials such as hydroxyethylcellulose can be dispersed in the mixture at room temperature to make a polymer solution, and heated up to above 70° C. When included in the composition, polyoxyethylene/polyoxyalkylene copolymer, amidoamines and acids, cationic surfactants, high melting point fatty compounds, and ester oils are added in the solution with agitation. Then, when included in the composition, inorganic heat generating agents such as magnesium sulfate are also added in the solution with agitation. The mixture thus obtained is cooled down to about 30° C., and the remaining components such as silicone compound are added with agitation.

Method of Use

The hair conditioning compositions of Examples 1 through 10 as shown above can be mixed with water and applied to the hair and/or skin by any conventional method well known in the art. For example, the anhydrous compositions can be applied to hair and/or skin after mixing with water on hands and/or in a certain vessel. The anhydrous compositions can be applied to wet hair and/or wet skin to mix with water remaining on the hair and/or skin. The anhydrous compositions can be applied to wet and/or dry hair and/or skin to mix with water when rinsed-off. The hair conditioning compositions of Examples 1 through 10 as shown above are preferably applied to wet hair to mix with water remaining on the hair.

The embodiments disclosed herein have many advantages. For example, the hair conditioning compositions of Examples 1 through 10 as shown above provide improved conditioning benefits such as moisturized feel, softness and smoothness. The hair conditioning compositions of Examples 1 through 10 as shown above warm to a temperature such that the user can perceive a warm feeling, when mixing with water. For example, the hair conditioning composition of Example 1 as shown above can warm up to a temperature of from about 30° C. to about 50° C., when applied to wet hair and mixed with water remaining on the hair.

It is understood that the examples and embodiments described herein are for illustrative purposes only and that various modifications or changes in light thereof will be suggested to one skilled in the art without departing from its spirit and scope.

What is claimed is:

1. A cosmetic composition which is anhydrous, and comprises:
   (a) from about 10% to about 40% of a hydrophobic polyol wherein the hydrophobic polyol is a polypropylene glycol having a molecular weight of from about 1000 to about 10,000;
   (b) from about 25% to about 75% of a hydrophilic polyol selected from the group consisting of propylene glycol, butylene glycol, hexylene glycol, glycerin, diglycerin, polyethylene glycol, and mixtures thereof;
   (c) from about 0.1% to about 20% of an oily conditioning agent wherein the oily conditioning agent is liquid at 25° C., and is a silicone oil; and
   wherein the weight ratio of the hydrophobic polyol to the hydrophilic polyol is in the range of from 1:2 to 1:10 and further wherein the cosmetic composition warms to a temperature of from about 25° C. to about 80° C. by mixing with water.

2. The cosmetic composition according to claim 1 further comprising an inorganic heat generating agent which generates a heat by mixing with water.

3. The cosmetic composition according to claim 2, wherein the inorganic heat generating agent is an anhydrous inorganic salt selected from the group consisting of sodium sulfate, calcium sulfate, magnesium sulfate, aluminum sulfate, calcium chloride, magnesium chloride, calcium oxide, and mixtures thereof.

4. The cosmetic composition according to claim 2, wherein the inorganic heat generating agent has an average diameter of from about 0.01 μm to about 40 μm.

5. The cosmetic composition according to claim 2 further comprising a polyoxyalkylene derivative.

6. The cosmetic composition according to claim 5, wherein the polyoxyalkylene derivative is selected from the group consisting of polyoxyethylene/polyoxypropylene copolymer, polyoxyethylene alkyl ether, polyoxypropylene alkyl ether, polyoxyethylene alkyl ether ester, polyoxypropylene alkyl ether ester, polyoxyethylene glyceryl ester, polyoxypropylene glyceryl ester, and mixtures thereof.

7. The cosmetic composition according to claim 1, which is an anhydrous hair care composition selected from the group consisting of an anhydrous hair shampoo composition, an anhydrous hair styling composition, an anhydrous hair conditioning composition, an anhydrous hair color composition, an anhydrous hair growth composition, and mixtures thereof.

8. The cosmetic composition according to claim 7, which is an anhydrous hair conditioning composition.

9. The cosmetic composition according to claim 7, wherein the anhydrous hair conditioning composition further comprises a cationic surfactant.

10. The cosmetic composition according to claim 8, wherein the anhydrous hair conditioning composition comprises by weight:
    (a) from about 10% to about 40% of the hydrophobic polyol;
    (b) from about 25% to about 75% of the hydrophilic polyol;
    (c) from about 0.1% to about 20% of the oily conditioning agent;
    (d) from about 0.1% to about 10% of a cationic surfactant;
    (e) from about 5% to about 60% of an inorganic heat generating agent which generates a heat by mixing with water; and
    (f) from about 0.1% to about 10% of a polyoxyalkylene derivative.

11. A method of conditioning hair comprising following steps:
    applying the hair conditioning composition according to claim 8 to wet hair;
    and mixing the hair conditioning composition with water remaining on the hair.

* * * * *